United States Patent [19]

Novack et al.

[11] Patent Number: 4,636,294

[45] Date of Patent: Jan. 13, 1987

[54] APPARATUS FOR DETECTING AND MEASURING HYDROGEN SULFIDE GAS IN THE PRESENCE OF CARBON MONOXIDE

[75] Inventors: Robert L. Novack, Evans City; Beth A. Tomasovic, New Kensington, both of Pa.

[73] Assignee: Bacharach, Inc., Pittsburgh, Pa.

[21] Appl. No.: 777,988

[22] Filed: Sep. 20, 1985

[51] Int. Cl.$^4$ ............................................. G01N 27/54
[52] U.S. Cl. ..................................... 204/432; 204/1 T
[58] Field of Search ............... 204/432, 1 F, 411, 412, 204/415, 431

[56] References Cited

U.S. PATENT DOCUMENTS

| | | | |
|---|---|---|---|
| 3,634,569 | 1/1972 | Emanuelson et al. | 264/105 |
| 3,801,374 | 4/1974 | Dews et al. | 136/120 |
| 3,859,138 | 1/1975 | Narsavage et al. | 136/120 |
| 3,912,538 | 10/1975 | Dews et al. | 136/86 D |
| 3,992,331 | 11/1976 | Petrow et al. | 252/472 |
| 4,001,103 | 1/1977 | Blurton et al. | 204/411 |
| 4,028,274 | 6/1977 | Kunz | 252/447 |
| 4,044,193 | 8/1977 | Petrow et al. | 429/40 |
| 4,127,462 | 11/1978 | Blurton et al. | 204/195 R |
| 4,313,972 | 2/1982 | Goller et al. | 427/113 |
| 4,326,927 | 4/1982 | Stetter et al. | 204/1 T |

Primary Examiner—G. L. Kaplan
Attorney, Agent, or Firm—Webb, Burden, Robinson & Webb

[57] ABSTRACT

The present invention discloses the use of gold oxide as a catalyst for use in a hydrogen sulfide gas detector. The gold oxide catalytic surface being supported on an electrically conductive substrate; thereby allowing the flow of electrons between the anode and the cathode to occur between the substrates of the electrodes instead of the catalytic surfaces. This will reduce the amount of catalytic material required to form the electrode, and will not require that the catalytic surface be an electrical continuum.

2 Claims, 2 Drawing Figures

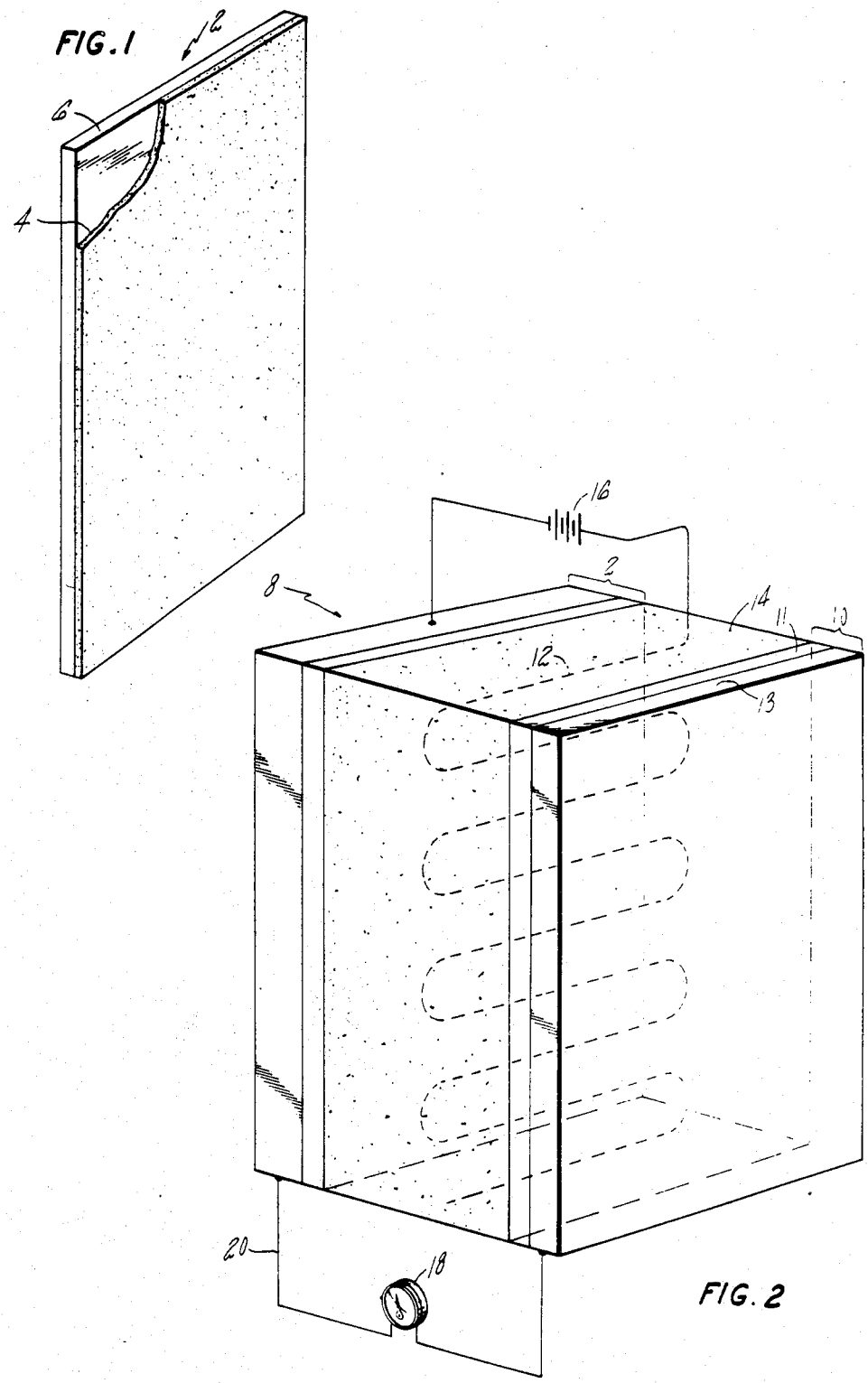

APPARATUS FOR DETECTING AND MEASURING HYDROGEN SULFIDE GAS IN THE PRESENCE OF CARBON MONOXIDE

DESCRIPTION

1. Technical Field

The technical field to which this invention pertains is electrochemical noxious gas detectors, in particular those detectors useful for detecting hydrogen sulfide.

2. Background Art

Electrochemical cells and electrolyte reactions have been used extensively to detect the presence of noxious gases in the atmosphere. These cells typically rely on an oxidation reaction of the specific gas to be detected at the anode, through the agency of a catalyst in the presence of an electrolyte, when a potential is impressed across the electrodes, thereby producing electrons and ions. The electrons are transmitted via an electrical wire to the cathode where, in the presence of a catalyst, the electrons are used in a reduction reaction with the ions produced at the anode. The amount of current flowing from the anode to the cathode is in direct relationship to the quantity of object gas present. The shortcoming of many of these noxious gas sensing cells is that they suffer from a lack of specificity. This means that many of these sensors react in the same fashion to a number of noxious gases, thereby generating false readings when one noxious gas is present with the object gas and both are detected by the sensor. One noxious gas mixture which has proven to be very difficult is that of hydrogen sulfide in the presence of carbon monoxide.

One solution which has been disclosed in U.S. Pat. No. 3,992,267 was the discovery that the reaction at the anode could be made specific through the regulation of the potential at that electrode. For instance, if the potential at that electrode was lower than the redox potential of the undesired reaction, then that component would not respond and therefore would not interfere with the detection of the object gas.

It has also been found that it is not only the potential placed on the anode which is the determining factor in the selectivity of the detector, but the composition of the catalyst used on the anode is also significant. U.S. Pat. Nos. 4,042,464 and 4,127,462 describe the use of a catalytic material comprising gold in the reduced metal state. This gold catalyst used on the anode offers greater selectivity to hydrogen sulfide gas in the presence of carbon monoxide. However, it has been found that these gold catalysts are expensive to manufacture due to the process of forming a gold oxide from a gold salt and then reducing the oxide to the pure metallic state. Additionally, the amount of gold required to form the anode was substantial as it was the electrical conductivity of the gold coated surface which allowed the flow of electrons produced by the reaction to migrate across the face of the anode to the collector plate. Another problem associated with this prior art of anode and cathode construction is that the collector plates and wires, which allow for the flow of electrons between the two electrodes, had to be placed on the face of each of the electrodes and thereby in contact with the corrosive electrolyte material. This caused two problems. First, the wires and collector plates must be made of corrosive resistant material due to the corrosive environment of the electrolyte, these materials are expensive and possibly rare, such as tantalum. Secondly, the need to have the wires and collector plates in the electrolyte cavity precludes the ability to totally seal the cavity and thereby prohibit the possibility of electrolyte leakage which might result around those points of entry of the wires into the cavity.

Therefore, what is needed in this art area are catalysts having comparable selectivity to that of the prior art yet are less expensive and less complicated to make, and allow for a flexibility of design so the electrolyte cavity may be sealed.

DISCLOSURE OF INVENTION

The present invention discloses an electrochemical gas detector having an anode and a cathode in contact with an aqueous ionic electrolyte or solid state ion membrane dispersed therebetween, and a reference electrode in electrical contact with the anode and the electrolyte. The critical difference between the present gas detector and those of the prior art is the use of gold oxide as the anodic catalyst and its dispersion onto an electrically conductive substrate. This allows for a design which incorporates the removal of the current from the anode substrate instead of the catalytic surface, as in the prior art. This catalyst has good selectivity to hydrogen sulfide, and similar sulfur compounds such as mercaptans, over hydrogen, carbon monoxide and other gases, and does not require the additional processing steps of reducing the oxide to the metallic state as the prior art requires. Additionally, since the catalyst is already in the oxide form, there is little likelihood that its efficiency will be impaired should a strong oxidizing gas be present during the analysis.

Other features and advantages will be apparent from the specification and claims and from the accompanying drawings which illustrate an embodiment of the invention.

BRIEF DESCRIPTION OF THE DRAWINGS

FIG. 1 is a cross section of the electrode of the present invention.

FIG. 2 is a schematic of the electrochemical cell utilizing the gold oxide catalyst.

BEST MODE FOR CARRYING OUT THE INVENTION

The gold oxide catalyst is produced by oxidizing a gold salt through exposure to traditional oxidizing conditions. The preferred starting material is gold hydroxide, however other gold salts which are oxidizable to gold oxide may be used. It should be noted that although it has not been determined by experimentation, it is believed that no residue from the gold salt, which could interfere with the activity of the gold oxide catalyst or the reduction reaction which takes place in its presence, should remain. Therefore, when using a gold salt such as a gold chloride, it is important that the chloride be removed from the catalyst prior to it being used. This may be accomplished by thoroughly washing the oxide with water, (for example, $Au(OH)_3$ can be precipitated and then washed to remove the chlorides).

The gold hydroxide is converted to gold oxide by placing it in an oven, in the presence of an oxidizing atmosphere, and heating until the water has been substantially (about 50 percent to about 100 percent) removed from the oxide, converting the hydroxide to the oxide form. Some oxide decomposition may occur but is reformed upon cooling in air. In the situation where the preferred material is used, it has been found that the gold hydroxide may be heated to about 300° F. (149° C.) for about 2 hours in an air atmosphere. Under these conditions, the hydroxide is substantially converted to the oxide form.

In addition to merely converting the gold to gold oxide, it is also important that the gold oxide catalyst have a high surface area, typically not less than 4 $m^2/gm$ and preferably greater than 10 $m^2/gm$. This will ensure high reactivity and selectivity in the resulting anode. The gold oxide should also be of a relatively fine mesh size in order to produce these large surface areas desired. Typically, this will range from about 0.1 microns to about 10 microns with the preferred being about 1.0 microns. It is also desirable that these gold oxide particles be porous in nature in order to further ensure an effective catalytic surface.

FIG. 1, which is meant to be exemplary and not limiting, is a schematic of a typical anode 2 of this invention. The gold oxide catalyst 4 is placed on a gas porous electrically conductive substrate 6. This substrate is typically a carbon paper formed of carbon or graphite fibers. These papers are conventional in the fuel cell art and must be electrically conductive. The preferred papers may be formed using conventional processes for producing graphite or carbon papers which are used in the fuel cell industry to act as substrates for the anodes and cathodes in electrochemical cells. A number of conventional methods which are useful in making these substrate papers are disclosed in U.S. Pat. Nos. 3,992,331; 3,933,684; 4,044,193 and 4,166,143.

Although it may not be necessary, it is preferred that the carbon papers be made hydrophobic through the impregnation with a hydrophobic material, most preferably a fluorinated polymer such as Teflon ® polymer. The impregnation process is again conventional. The preferred papers should be about 5 mils to about 20 mils thick with about 12 to about 15 mils being most preferred. These papers should also contain about 30% to about 50% by weight of Teflon polymer with an optimum of about 38% by weight preferred. It has been found that too little Teflon polymer will not offer sufficient hydrophobicity to the paper, while too high a content will produce unacceptably high electrical resistance between the paper and the catalytic layer.

Other electrically conductive substrates may be used such as carbon felts or porous carbon boards or even electrically conductive polymers such as polyacetylene, all of which may be made hydrophobic through the same impregnation technique as utilized with the carbon or graphite electrodes.

After the carbon paper has been Teflon polymer impregnated, the gold oxide catalytic layer is applied. As with the carbon papers, it is preferred that the gold catalytic layer be made hydrophobic, thereby preventing the electrolyte from penetrating too deeply into the catalyst and forming a film to prevent gas permeation to the electrolyte/catalyst interface. Therefore, prior to the gold oxide being applied to the paper, it is mixed with a hydrophobic material such as Teflon polymer to form an aqueous slurry. The slurry typically contains about 15% to about 30% by weight of hydrophobic material. The hydrophobic material should be colloidal in nature. A preferred material is DuPont #30 TFE suspension available from DuPont Corporation, Wilmington, Del. The slurry is mixed thoroughly to insure satisfactory homogeneity and then applied to the hydrophobic papers. The method of applying this catalytic layer is conventional, such as applying it with a spatula or roller or other technique as long as it is applied uniformly. The catalyst should be applied to a thickness of about 1–4 mils with a gold oxide loading of about 5 $mg/cm^2$ to about 30 $mg/cm^2$, and may comprise from about 25% to about 85% by weight of the catalytic layer. Since the use of the electrically conductive substrate in these electrodes, there is no need to have each catalytic particle be in electrical contact with every other catalytic particle forming an electrically continuous surface to conduct the current across, less catalytic material need be present resulting in lower catalytic loading rates and reducing the cost of the electrode. In addition, since these electrodes allow front to back conduction of the current, it allows for a number of design and construction changes not before available in the art. One of these changes is that the collector plates, which conduct the electricity from one electrode to the other electrode, may now be placed directly on the back of each electrode, thereby removing these collector plates from contact with the caustic or corrosive electrolyte. Again, this allows for the use of less expensive materials to form the collector plate as they will no longer need to be resistant to attack from the electrolyte in this design. A second feature, which is a result of the use of these electrodes, is the fact that the electrolyte cavity may now be completely sealed since the collector plates and attendant wires no longer have to enter or exit the electrolyte cavity to make electrical contact between both electrodes. This avoids any sealing problems around these wires and therefore reduces any potential leakage which could prematurely destroy the sensor. Although the catalyst may be applied in a single application, it is preferred that a number of applications be used until a preferred loading in the 5–30 $mg/cm^2$ is achieved. In certain instances, particularly where the low catalytic loadings are used, it may be desirable to mix the gold oxide catalyst with a diluent such as carbon powder along with the Teflon polymer. This carbon powder diluent will aid in improving the bonding of the catalytic layer to the substrate.

Once the catalyst has been placed on the paper, the structure is placed in an oven and sinter bonded. Typically this is done at temperatures of about 527° F. (275° C.) to about 617° F. (325° C.) for about 15 minutes to about 1 hour. The sintering procedure causes the Teflon polymer in the catalytic layer to bond or fuse with the Teflon polymer of the substrate to securely bond the catalytic layer to the substrate.

After the electrode material has been sintered, it is removed from the oven and cooled. The electrode material is then cut into the desired shapes to form the anode which will be used in the gas detector cell.

The electrode material having been cut into its proper shape is then fitted together with the other principal components to form the sensing cell. A more complete description of the cell may be found below.

FIG. 2 which is a schematic of a conventional electrolytic noxious gas detector cell of the type useful in the present invention, is meant to be exemplary only and not limiting.

The anode 2 is placed in an electrochemical detector cell 8 having a cathode 10, comprising a catalytic layer 11 and an electrically conductive substrate 13, a reference electrode 12, a means of maintaining a substantial constant potential 16 between the reference electrode 12 and the anode 2 and an ionic (solid or liquid) electrolyte 14 dispersed between the anode 2 and the cathode 10. The anode 2 and the cathode 10 are connected electrically by means of a wire 20 which allows a path for the flow of electrons from the anode to the cathode during operation. In addition, a means for measuring the flow of electrons 18 due to the oxidation reaction taking place at the anode when the object gas is being analyzed is shown in block diagram form as it is conventional and need not be depicted in detail.

Cathodes conventional in this art (e.g. such as referred to in the Background section) can be used. However, it is preferred that the cathode be prepared in a similar fashion as that used to prepare the anode wherein the catalytic material, typically platinum, is mixed with a hydrophobic material, i.e. Teflon polymer and placed on the same electrically conductive, hydrophobic substrate as the anode. The catalyst layer is then bonded to the substrate through the same sintering process as was used to prepare the anode. This sintering operation is typically done in air. The Pt is purchased as Pt black, fuel cell grade, and no effort is made to guard against platinum oxide formation during the sintering process.

The reference electrodes which may be used are conventional and can be the same as the cathode electrode, i.e. a gas diffusion electrode, which is shielded from exposure to the object gases of interest. In addition, the reference electrode may be comprised of a platinum catalyzed wire immersed in the electrolyte as is shown in FIG. 2. This wire may be any platinum black coated electrochemically inert, electrically conductive wire having a diameter of about 5 to about 15 mils. The wire is preferably made of platinum but other materials such as rhodium or gold may also be used. Although it is preferred that these wires be coated with a platinum black, other conventional coatings which may be used would be those of palladium, iridium, ruthenium, osmium, etc. In addition, it may also be possible to use sacrificial reference electrodes such as silver or reference electrodes comprising a carbon yarn coated with platinum black or other coating.

The anode is positioned such that the catalytic surface 4 (that surface containing the gold oxide or first face) is contacting the electrolyte 14 as shown in FIG. 2. The cell housing (not shown) has a means for allowing the object gas to contact the other surface of the anode (second face)(not shown). The electrolyte used may be any conventional aqueous ionic electrolyte such as sulfuric acid, phosphoric acid or base such as potassium hydroxide. Additionally, the electrolyte may also be in the form of a solid polymer electrolyte which comprises an ionic exchange membrane. These electrolytes may be in the form of a free liquid, they may be entrapped in a matrix or slurry such as glass fibers, or they may be solid gels.

The theory and operation of the electrochemical gas detector units of the present invention is conventional. The key differences are the use of a non-electrically conductive gold oxide catalyst dispersed onto an electrically conductive carbon substrate, which allows for the use of less catalyst due to the fact that the face of the anode or cathode need not be electrically conductive as it is not used as the electron collector. Instead of the electrons being collected across the face of these electrodes as in the prior art, they are conducted through the electrically conductive carbon substates, each substrate being in contact with the other through wire leads, thereby allowing the total sealing of the electrolyte cavity which is not otherwise been available to designers.

The detection units utilizing the gold oxide anodes of the present invention were tested in hydrogen sulfide environments in the presence of carbon monoxide and the following are examples and results of that testing.

EXAMPLE I

A test cell was made using an anode of gold oxide prepared as described above. The anode was circular in shape and 0.480 inch in diameter. The catalytic paper substrate was 12 mils thick and was formed of carbon containing about 38 percent by weight of Teflon polymer. The catalytic layer was 2-3 mils thick and contained about 80 percent by weight of gold oxide with the balance Teflon polymer. The cathode was a conventional platinum cathode also formed in a circular fashion with the same diameter and a thickness of 12-15 mils. The aqueous electrolyte was 55 percent phosphoric acid and a conventional air reference electrode was used to maintain a substantially constant potential between the reference electrode which was a platinum black coated platinum wire, and the anode.

A comparison was made between a gold catalyst anode, a platinum anode and a gold oxide catalyst to determine how the cells responded to a known quantity of $H_2S$ gas. The cells were operated at a bias potential of 150 mv relative to the reference electrode and the test comprised determining the response of the anode to an $H_2S$ gas at a known concentration as well as its response to a gas of known concentration of carbon monoxide. As can be seen in the resulting table, the platinum anode performed poorly as it reacted quite positively to the CO indicating the presence of $H_2S$ in the sample object gas. However, both the gold and gold oxide cells performed similarly with similar CO rejection ratios.

TABLE

| | Anode Bias Potential | $\mu$A/ppm CO | $\mu$A/PPM $H_2S$ |
|---|---|---|---|
| Platinum Cell | 150 mv | .10 | 1.29 |
| Gold Cell | 150 mv | .00 | .20 |
| Gold Oxide Cell | 150 mv | .00 | .23 |

It should be understood that the invention is not limited to the particular embodiments shown and described herein, but that various changes and modifications may be made without departing from the spirit and scope of this novel concept as defined by the following claims.

We claim:

1. An apparatus for the detection and measurement of hydrogen sulfide gas in an object gas comprising
   (a) an anode having an electrically conductive substrate with a gold oxide catalyst dispersed thereon,
   (b) a cathode having an electrically conductive substrate having a cathodic catalyst dispersed thereon wherein the anode and cathode are in electrical contact with one another,
   (c) an electrolyte dispersed between, and in contact with, the anode and the cathode,
   (d) a reference electrode in contact with the electrolyte and the anode,
   (e) a means for supplying and maintaining an electrical potential from about 0 to about 300 mv, between said anode and said reference electrode; and
   (f) a means for measuring the current flow from said anode to said cathode which current is a measure of the concentration of the hydrogen sulfide.

2. The method of claim 1 wherein the catalyst comprises about 10 percent to about 85 percent by weight gold oxide dispersed on hydrophobic carbon.

* * * * *